United States Patent [19]

Seike et al.

[11] 4,331,731
[45] May 25, 1982

[54] EXOTHERMIC BODY

[75] Inventors: Takashi Seike, Yokohama; Takehiko Kobayashi, Tokyo, both of Japan

[73] Assignee: Mitsubishi Gas Chemical Company, Inc., Tokyo, Japan

[21] Appl. No.: 287,623

[22] Filed: Jul. 28, 1981

[30] Foreign Application Priority Data

Aug. 1, 1980 [JP] Japan .................. 55-106146

[51] Int. Cl.$^3$ .................. B32B 3/26; A43B 7/02; A43B 3/10
[52] U.S. Cl. .................. 428/305.5; 36/44; 36/87; 36/2.6; 428/316.6; 428/317.9; 44/1 R; 44/3 A
[58] Field of Search .................. 36/2.5, 44; 428/71, 428/76, 305.5, 316.6, 317.9

[56] References Cited

U.S. PATENT DOCUMENTS

| | | | |
|---|---|---|---|
| 3,493,986 | 2/1970 | Erwin | 36/2.6 |
| 3,960,628 | 6/1976 | Snyder | 156/133 |
| 4,023,282 | 5/1977 | Ziegelheafer | 36/2.6 |
| 4,094,080 | 6/1978 | Sanders | 36/2.6 |
| 4,146,415 | 3/1979 | Caretta et al. | 156/133 |
| 4,249,319 | 2/1981 | Yoshida | 36/2.6 |

FOREIGN PATENT DOCUMENTS

| | | | |
|---|---|---|---|
| 967000 | 5/1975 | Canada | 36/2.6 |
| 1299622 | 6/1962 | France | 152/361 FP |

*Primary Examiner*—William J. Van Balen
*Attorney, Agent, or Firm*—Koda and Androlia

[57] ABSTRACT

The present invention provides an exothermic body for use of an insole of shoes and so forth with elasticity, softness and flexibility, the exothermic heat of which is distributed uniformly along the entire area thereof. The exothermic body includes a foamed plastic sheet having cells therein, the cells being filled with an exothermic agent such as a mixture of iron, saline solution, activated carbon and woodmeal or pulp powder. The foamed plastic sheet is covered by an air-permeable thin film such as a thin perforated plastic film. A cushion material is provided on at least one surface of the foamed plastic sheet covered with the air-permeable thin film and the foamed plastic sheet together with the cushion material is covered by an air-permeable film cover.

13 Claims, 2 Drawing Figures

EXOTHERMIC BODY

BACKGROUND OF THE INVENTION

1. Field of the Invention

This invention relates to an exothermic body, and more particularly to an elastic, soft and flexible exothermic body having its core of a foamed plastic covered with an air-permeable thin film, cells of the foamed plastic being filled with a chemical heat generating agent or exothermic agent (hereinafter, referred to exothermic agent).

2. Description of the Prior Art

It is very uncomfortable to wear cold shoes for a long time in a cold environment, and it may also cause a disease. There has been, however, no effective warming insole in order to prevent such discomfort.

On the other hand, arthritic, neuralgic or rheumatic patients and the like feel an acute pain in their affected parts of their body in winter, so that they suffer from a serious pain. In this respect, it is necessary to warm up these affected parts in order to abate such pain. However, there has never been a suitable warming implement for simply and easily warming up such affected parts which are either severly bent and moved as in a joint and the like, or extending over a wide area.

A lot of simple, safety and energy-conservation type warming implements utilizing an exothermic agent have recently been employed in place of warming implements utilizing methanol and benzine as well as pulverized coal etc. as fuels, and another type of warming implements in which a battery is used. In such energy-conservation type warming implement, heat is generated by reacting, with oxygen, exothermic agent being a mixture of an easily oxidizable material such as iron power or sodium sulfide, carbon as a catalyst, and saline solution as an oxidation accelerator.

In such type of warming implement, however, the exothermic agent is contained in a bag in a powdery or slurry form, and in addition, a volume of the bag is considerably larger than that of the exothermic agent to facilitate a contact with oxygen. Accordingly, the exothermic agent freely transfers in the bag in accordance with deformation, transference and reversal or the like of the warming implement, so that the agent is unevenly distributed in the bag and the distribution of exothermic heat becomes uneven in the entire warming implement. Further, when such warming implement is pressed, the agent does not sufficiently contact with oxygen because of lack of breathability, thereby generating insufficient heat, or when the implement becomes solid, such implement does not generate heat any more, even if such pressure is removed after the implement was once made to be solid. For these reasons, satisfactorily warming implements have never been proposed heretofore.

SUMMARY OF THE INVENTION

The present inventors contemplate to eliminate disadvantages as mentioned above in a conventional warming implement in which an exothermic agent is utilized. It is an object of the present invention to propose a novel elastic, soft and flexible warming implement by which an even distribution of exothermic heat can be obtained by preventing the exothermic agent from consisting unevenly in accordance with deformation, transference and reversal or the like of the warming implement. As a result of their eager studies upon the above matters, the present inventors have achieved this invention.

More specifically, the present invention relates to an exothermic body in which a foamed plastic sheet, cells of which are filled with an exothermic agent, is covered with an air-permeable thin film to fix on the surfaces of the foamed plastic sheet to prepare a core, a cushion material is further placed on at least one surface of the aforesaid core, and moreover, the resulting core and a cushion material are covered with an air-permeable film cover.

DESCRIPTION OF THE PREFERRED EMBODIMENT

Figure 1:
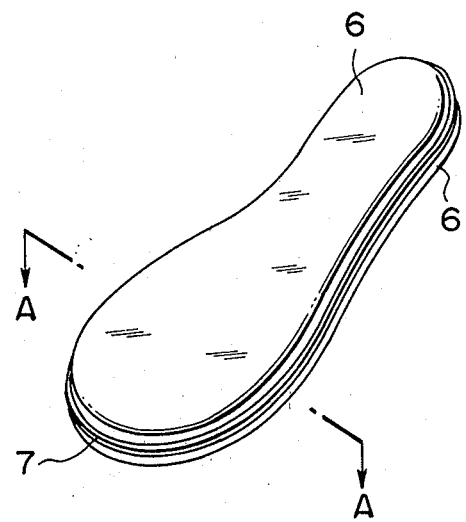
FIG. 1 is a perspective view showing an exothermic body according to the present invention being utilized as an insole for a shoe.

The exothermic agent to be utilized in the present invention may be a material which easily reacts with oxygen in the air to generate heat at the time of this reaction. Although such material should not be particularly limited, usually the material is preferred to be a mixture of an oxidizable substance(s) such as pure iron, reduced iron, nickel, sodium sulfide and/or sodium sulfite etc.; an oxidation accelerator(s) such as common salt, calcium chloride, magnesium chloride and/or mineral acid and water etc.; and a catalyst such as activated carbon, carbon power and a mixture consisting of copper compound and manganese compound etc.; and further, if necessary, ethylene glycol as well as a water retaining agent or diluent such as powdery cellulose substances, for example, woodmeal, pulp powder, powdery straw etc. In these mixtures, preferable is the one consisting of pure iron or reduced iron, saline solution, activated carbon and woodmeal or pulp powder. It is preferable that each size of these materials is the one passing through 48 mesh (Tyler mesh) of standard sieve. Furthermore, when cells of a foamed plastic sheet are filled with an exothermic agent, generally 1 $cm^3$ of the foamed plastic sheet may be filled with 0.5–1.5 g of the exothermic agent in practical use.

The foamed plastic sheet employed for this invention may be an elastic and flexible open-cell foamed plastic having a so-called three dimensional structure, and the specific examples of materials of which include, for example, polyurethane, synthetic rubber, crosslinked polyvinyl chloride and polyethylene etc. The most preferable is polyurethane among these materials. In general, the foamed plastic sheet having a thickness of 2–3 mm, an average cell population of 15–25/25 mm, an average cell diameter of 0.5–1.0 mm and a percentage of open-cell of 75% or more is preferably used in the present invention.

The air-permeable thin film in the present invention may be such film which can promptly discharge and charge air in accordance with the application and removal of pressure onto or from the foamed plastic sheet and has an air-permeability of such an extent through which the exothermic agent cannot pass. Specific examples of the air-permeable thin film include perforated plastic thin films, and woven or non-woven fabrics made of synthetic or natural fibers. Either an air-permeable thin film the whole surface of which has air-permeability; or a thin film having air-permeability only on the area corresponding to that of one side of the foamed plastic sheet may be used. Generally, a non-woven fabric made from a natural and/or synthetic fiber(s) is employed in the invention. In this case, a weight of non-woven fabric per unit area is usually within a range of 30–100 g/m². As a matter of course, a perforated plastic thin film may also be utilized. Such air-permeable thin film is fixed on the surface of the foamed plastic sheet in such that the exothermic agent in the cells does not leak out from the inside of the cells to the surface of the foamed plastic sheet at the time of deforming, transferring or reversing and the like of the foamed plastic sheet. The fixing of the air-permeable thin film onto the surface of the foamed plastic sheet is effected by means of whole or partial sewing, paste bonding, adhesive bonding or heat fusing etc., and adhesive bonding or heat fusing is preferable in practical use, further the most preferable is heat fusing from the viewpoints of safety in the operations and control of environmental pollution. In case of adhesive bonding, an adhesive to be employed may be the one which retains flexibility after curing the same and which may be either solvent type or emulsion type and in which, for example, vinyl acetate, synthetic rubber, acrylic resin or the like may be utilized. On the other hand, heat fusing is carried out by means of impulse or dielectric heat sealing.

Moreover, the covering of the foamed plastic sheet with air-permeable thin films is carried out by such manner that the air-permeable thin films having a slightly smaller or larger size than the planar dimension of the foamed plastic sheet are fixed on both surfaces of the foamed plastic sheet, and the peripheral portions of the air-permeable thin films are firmly sealed. Such firm sealing of the air-permeable thin films is effected by means of paste bonding, adhesive bonding or heat fusing similar to the case of fixing the air-permeable thin film onto the foamed plastic sheet.

In order to effect the firm sealing of the air-permeable thin films by means of heat fusing, it is required that either at least peripheral portions of the air-permeable thin films are made from a thermoplastic synthetic resin such as polyamide, polypropylene, polyethylene or acrylic resin, etc., or layers of such thermoplastic synthetic resins as mentioned above are provided on at least peripheral portions of the air-permeable thin films.

Furthermore, in the case of fixing the air-permeable thin film on the surfaces of the foamed plastic sheet by means of heat fusing, such air-permeable thin films are made from the thermoplastic synthetic resins as set forth above or a non-heat-fusible film. The non-heat-fusible film is, for example, a non-woven or woven fabric made of, e.g., a natural fiber, on the entire or part of the surface of which the thermoplastic synthetic resin layer is provided. In case of such non-woven or woven fabric without thermoplastic synthetic resin layer at the time of such heat fusing, it is necessary that the non-woven or woven fabric involves 40% by weight or more of a thermoplastic synthetic resin fiber.

Cells of the foamed plastic sheet are filled with the exothermic agent by such manner that either the exothermic agent is rubbed over the surface of the foamed plastic sheet onto which the air-permeable thin film has not been fixed and on the other side of which the film has been fixed, or the exothermic agent is placed on the surface of the aforesaid side of the foamed plastic sheet and then, vibration is applied on the resulting foamed plastic sheet. In practical use, preferable is to fill cells of the foamed plastic sheet with the exothermic agent by means of vibration.

As stated above, the foamed plastic sheet, the cells of which are filled with the exothermic agent, is covered with air-permeable thin films to obtain a core. In this case, it is preferable that the resulting core has air-permeability at both sides thereof, but the core may have air-permeability in only either side thereof.

Further a cushion material is put on the side with air-permeability of the core, or two cushion materials are placed on both sides of the core, and then the outside of the core provided with the cushion material on one side or both sides thereof is covered with air-permeable film covers to obtain an exothermic body.

Such cushion material as mentioned above is used for effecting more smoothly discharge and charge of air accompanied with the application and removal of pressure onto or from the foamed plastic sheet to further elevate follow-up action of the exothermic body in accordance with variation of external force. Such cushion material is not particularly specified except that the cushion material has elasticity, flexibility and air-permeability. Specific examples of the cushion material usualy include felt, open-cell foamed plastic sheet and the like, and among these materials, the most preferable is open-cell foamed plastic sheet. An example of the material for the open-cell foamed plastic sheet includes polyurethane, synthetic rubber, ethylene-vinyl copolymer, flexible polyvinyl chloride. In this case, the open-cell foamed plastic sheet having a percentage of open-cell of 30% or more and a thickness of 2–5 mm is preferably used.

The air-permeable film cover for covering the core and cushion material(s) requires also air-permeability with such an extent that a smooth discharging and charging of air can be effected in response to application and removal of pressure onto or from the foamed plastic sheet. Specific examples of the air-permeable film cover include a thermoplastic synthetic resin film prepared from a synthetic resin such as polyamide, polyolefin, acrylic resin or the like; woven or non-woven fabrics made of such thermoplastic synthetic resins as described above, natural fibers or the combination of the thermoplastic synthetic resin fibers with natural fibers; or the one obtained by providing a synthetic resin film on the surface of any of the above stated woven and non-woven fabrics. In general, a woven or non-woven fabric on the surface of which a thermoplastic synthetic resin film or synthetic resin film is provided is perforated in order to afford air-permeability to the film. Such perforating operation may be performed in any stage such as prior to, at the time of production of the exothermic body or immediately before practical use of the exothermic body. Each size of holes of the air-permeable film cover is not particularly restricted, but generally a size of around 50–100$\mu$ is practically adopted. Moreover, a thickness of the air-permeable film cover varies depending upon the material thereof, but it is sufficient for generally around 0.1–0.3 mm in practical use.

It is preferable that the outermost layer of the exothermic body has air-permeability in both sides thereof, but the air-permeability in only either side of the outermost layer of the exothermic body may also be acceptable.

In one embodiment, the core is put on the cushion material. One of the air-permeable film covers each having a slightly larger size than the planar dimension of the core is put on an upper surface of the core as well as the other air-permeable film cover is placed under the bottom surface of the cushion material, and the peripheral portions of the air-permeable film covers are firmly sealed by means of sewing, paste bonding, adhsive bonding or heat fusing as mentioned above to cover the core and cushion material with the air-permeable film covers. In this case of firm sealing, the adhesive bonding or heat fusing is preferable, and particularly preferable is heat fusing from industrial point of view.

Before using actually, the exothermic body, the outermost layer of which has air-permeability, must be contained in an impermeable container or sealed from the atmosphere by applying an adhesive paper thereon, in order that the exothermic agent in the exothermic body is out of contact with the air.

A shape of the exothermic body according to the present invention may be varied in accordance with the use thereof.

The invention will be more specifically described hereinbelow by referring to the accompanying drawings.

Figure 2:
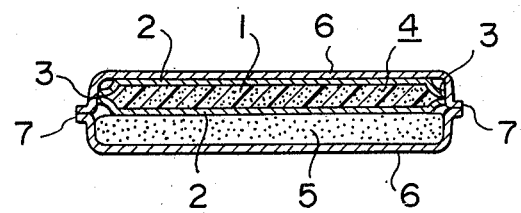
FIG. 2 is a cross-sectional view showing the exothermic body taken along line A—A of FIG. 1.

That is, FIG. 1 is a perspective view showing an insole for a shoe made of an exothermic body according to this invention, and FIG. 2 is a cross-sectional view showing the insole of the exothermic body taken along line A—A of FIG. 1.

Referring to FIGS. 1 and 2, two air-permeable thin films 2 and 2 are fixed on both surfaces of a foamed plastic sheet 1, cells of which are filled with an exothermic agent, and the peripheral portions 3 and 3 of the air-permeable thin films 2 and 2 are firmly sealed to each other to cover the foamed plastic sheet 1, thereby obtaining a core 4. A cushion material 5 is placed on a surface of the core 4, expecially under a bottom surface of the core 4. Air-permeable film covers 6 and 6 are put on the upper surface of the core 4 and on the bottom surface of the cushion material 5, respectively. Then the peripheral portions 7 and 7 of the air-permeable film covers 6 and 6 are firmly sealed to each other to cover the core 4 as well as cushion material 5, thereby producing the exothermic body.

The exothermic body according to the present invention retains a remarkable lasticity, softness and flexibility for a long period of time, and the distribution of temperature is always uniformal along the entire area of the exothermic body. Accordingly, the exothermic body of the present invention is preferably utilized for insoles of shoes, warming implements for flexing portions and wide area, and a pad for a face of human body, etc.

What is claimed is:

1. An exothermic body comprising:
   a foamed plastic sheet having cells therein;
   an exothermic agent filled in said cells;
   an air-permeable thin film fixed on a surface of said foamed plastic sheet and covering said foamed plastic sheet;
   a cushion material provided on at least one surface of said foamed plastic sheet covered with said air-permeable thin film; and
   an air-permeable film cover covering said foamed plastic sheet and said cushion material in layer.

2. An exothermic body as set forth in claim 1, wherein said exothermic agent is a mixture comprising an oxidizable substance, an oxidation accelerator, a catalyst, and a water retaining agent or diluent.

3. An exothermic body as set forth in claim 1 or 2, wherein said exothermic agent contains at least iron.

4. An exothermic body as set forth in claim 1 or 2, wherein said exothermic agent is a mixture comprising iron, saline solution, activated carbon and woodmeal or pulp powder.

5. An exothermic body as set forth in claim 1, wherein said foamed plastic sheet is an open-cell foamed sheet having a three dimensional structure.

6. An exothermic body as set forth in claim 1 or 5, wherein said foamed plastic sheet is made from polyurethane, synthetic rubber, crosslinked polyvinyl chloride or polyethylene.

7. An exothermic body as set forth in claim 1, wherein said air-permeable thin film is a thin perforated plastic film, or a woven or non-woven fabric prepared from synthetic or natural fibers.

8. An exothermic body as set forth in claim 7, wherein a peripheral portion of said air-permeable thin film is provided with a thermoplastic synthetic resin.

9. An exothermic body as set forth in claim 1 or 8, wherein a pair of said air-permeable thin film is put on both surfaces of said foamed plastic sheet and said peripheral portion of said air-permeable thin film is fixed each other by heat fusing.

10. An exothermic body as set forth in claim 1, wherein said cushion material is a felt on an open-cell foamed sheet.

11. An exothermic body as set forth in claim 1 or 10, wherein said cushion material is an open-cell foamed sheet prepared from polyurethane, synthetic rubber, ethylene-vinyl copolymer or flexible polyvinyl chloride.

12. An exothermic body as set forth in claim 1, wherein said air-permeable film cover is:
   a thermoplastic synthetic resin film with air-permeability;
   a woven or non-woven fabric prepared from thermoplastic synthetic resin fibers and/or natural fibers; or
   an air-permeable film prepared from a woven or non-woven fabric with thermoplastic synthetic resin thereon.

13. An exothermic body as set forth in claim 12, said thermoplastic synthetic resin is polyamide, polyolefin or acrylic resin.

* * * * *